(12) United States Patent
Jessop

(10) Patent No.: US 10,029,952 B2
(45) Date of Patent: Jul. 24, 2018

(54) COMPOSITIONS FOR GROWTH AND VIGOUR IN SOYBEAN

(75) Inventor: Nicholas Hugh Hylton Jessop, Winchester (GB)

(73) Assignee: Exosect Limited, Winchester, Hants (GB)

( * ) Notice: Subject to any disclaimer, the term of this patent is extended or adjusted under 35 U.S.C. 154(b) by 390 days.

(21) Appl. No.: 14/112,837

(22) PCT Filed: Apr. 19, 2012

(86) PCT No.: PCT/GB2012/000364
§ 371 (c)(1),
(2), (4) Date: Nov. 12, 2013

(87) PCT Pub. No.: WO2012/143682
PCT Pub. Date: Oct. 26, 2012

(65) Prior Publication Data
US 2014/0109636 A1    Apr. 24, 2014

(30) Foreign Application Priority Data

Apr. 20, 2011 (GB) .................................. 1106759.2

(51) Int. Cl.

| | |
|---|---|
| *C05B 17/00* | (2006.01) |
| *A01N 25/00* | (2006.01) |
| *A01N 25/08* | (2006.01) |
| *C05D 9/02* | (2006.01) |
| *C05F 11/08* | (2006.01) |
| *C05F 11/10* | (2006.01) |
| *C05G 3/00* | (2006.01) |
| *C09D 191/06* | (2006.01) |
| *C09D 5/03* | (2006.01) |

(52) U.S. Cl.
CPC .............. *C05B 17/00* (2013.01); *A01N 25/00* (2013.01); *A01N 25/08* (2013.01); *C05D 9/02* (2013.01); *C05F 11/08* (2013.01); *C05F 11/10* (2013.01); *C05G 3/0035* (2013.01); *C09D 5/031* (2013.01); *C09D 191/06* (2013.01); *C08L 2205/18* (2013.01)

(58) Field of Classification Search
CPC ........ A01N 25/08; A01N 25/00; C05B 17/00; C05G 3/0035

USPC .......................................................... 47/57.6
See application file for complete search history.

(56) References Cited

U.S. PATENT DOCUMENTS

| | | | |
|---|---|---|---|
| 2,936,226 A | 5/1960 | Kaufman et al. | |
| 3,096,171 A * | 7/1963 | Woerther | C05G 3/0035 252/384 |
| 3,905,152 A * | 9/1975 | Loperfido | A01C 1/06 47/57.6 |
| 4,020,200 A * | 4/1977 | Groszek | B63B 59/04 106/18.28 |
| 4,735,017 A * | 4/1988 | Gago | A01C 1/06 427/4 |
| 5,283,060 A | 2/1994 | Shieh | |
| 5,525,131 A * | 6/1996 | Asano | A01C 1/06 47/57.6 |
| 2003/0108584 A1 | 6/2003 | Priesnitz et al. | |
| 2005/0065034 A1* | 3/2005 | Miele | C05G 3/0035 504/367 |
| 2007/0072775 A1 | 3/2007 | Van Boxtel-Verhoeven et al. | |
| 2007/0207927 A1 | 9/2007 | Rosa et al. | |

FOREIGN PATENT DOCUMENTS

| | | |
|---|---|---|
| EP | 2 229 808 A1 | 9/2010 |
| GB | 2 118 158 A | 10/1983 |
| WO | 99/07654 A1 | 2/1999 |
| WO | 01/78509 A2 | 10/2001 |
| WO | 2005/077169 A1 | 8/2005 |
| WO | WO 2010107312 A1 * | 9/2010 ............... A01C 1/06 |

OTHER PUBLICATIONS

"Wax", Wikipedia XP-002688447, Nov. 25, 2011, http://en.wikipedia.org/wiki/Wax.
Search Report for GB 1206967.0 dated Aug. 17, 2012.
International Search Report for PCT/GB2012/000364 dated Apr. 10, 2013.

* cited by examiner

*Primary Examiner* — Joshua D Huson
(74) *Attorney, Agent, or Firm* — Sughrue Mion, PLLC

(57) ABSTRACT

Coating composition for applying to soybean seed from which roots and shoots are capable of growing, wherein the said coating composition comprises one or more organic materials having a melting point of ≥50° Centigrade and one or more additives, methods of making such compositions and coated soybean seeds.

6 Claims, No Drawings

COMPOSITIONS FOR GROWTH AND VIGOUR IN SOYBEAN

CROSS REFERENCE TO RELATED APPLICATIONS

This is a National Stage of International Application No. PCT/GB2012/000364, filed Apr. 19, 2012, claiming priority from British Patent Application No. 1106759.2, filed Apr. 20, 2011, the contents of all of which are incorporated herein by reference in their entirety.

The present invention relates to coating compositions including an organic component for applying to soybean seeds from which roots and shoots are capable of growing, uses of coating compositions on soybean seeds, methods of producing such coating compositions and soybean seeds coated with such coating compositions. In particular, the invention relates to coating compositions that comprise an organic material and at least one additive that enhances plant growth and/or plant vigour.

Young soybean plants grown from seed are vulnerable to abiotic and environmental stresses, particularly in growing habitats that have low rainfall and/or sub-optimal soil quality. Losses due to sub-optimal soil quality are typically realised in the growth of young plants lacking plant vigour in which the plants do not become well established, such as where the rooting systems do not develop and in circumstances where essential elements in the soil are not readily available. Agronomic losses due to young soybean plants not being well established remain unacceptably high on soils which are for example mineral deficient despite the employment of conventional inorganic seed coatings that typically include essential elements for establishing young seedlings. A problem with the use of such conventional seed coatings is that they introduce nutrients to the soil in unbalanced quantities and this can have adverse effects on plant growth and vigour in unforeseen ways. Additionally, such conventional coatings are typically applied in the form of wet slurries to soybean seeds. Once applied, the coatings are typically dried on the seeds and this drying may cause further abiotic stress to soybean seed, which in turn may have deleterious consequences on the viability of young plants grown from such seed. Additionally, such conventionally applied coatings may not be applied to soybean seeds evenly, and as a consequence, such coatings tend to be susceptible to chipping and/or flaking. Furthermore, the degree of coating uniformity over seeds of such conventionally applied coatings typically is not optimal, with a percentage of seeds of any one batch receiving little or no coating depending on the coating method being deployed.

In the following description, the terms "seed treatment" and "seed coating" are used interchangeably for the compositions of the invention and their uses to treat seeds by any of the specific methods described in the prior art that provide an improvement, typically an enhancement, of seedling vigour. The commonly used ingredients in seed treatment compositions (sometimes designated as formulations) include antidotes and safeners; fertilisers, micronutrients and inoculants; bioregulators of natural or synthetic origin which are either hormones or interfere in hormone metabolism and do not influence plant nutrition; and/or bioregulators which interfere with plant growth by enhancing nutrient uptake.

It has now been found that by using certain organic materials as components of coatings on soybean seeds, together with the application of inorganic components and/or biological agents, plant vigour and plant growth of plant seedlings grown from soybean seeds is improved relative to the plant vigour and plant growth of seedlings grown from conventionally treated soybean seeds. It has further been found that the quantity of additives, particularly inorganic fertilisers that is required per unit of seed weight is less than that required using conventional farming techniques.

It is an object of the present invention to supply improved seed coatings comprising organic components for soybean seeds.

It is a further object of the present invention to provide improved seed coatings comprising a minimum amount of additives.

These and other objects of the invention will become apparent from the following description and examples.

According to the present invention there is provided a soybean seed coating composition, wherein the said coating composition comprises i) at least one organic material selected from waxes having a melting point of $\geq 50°$ Centigrade; and ii) at least one additive for enhancing seedling vigour and/or seedling growth from soybean seeds wherein the at least one additive is selected from one or more inorganic additives and/or one or more live biological agents.

The organic materials of use in the invention act as a carrier for desired additives for placing on or near to seeds.

Commercial growers of soybean require seeds for the provision of new plants for building up seed stocks for sale to farmers. For the purposes of the present invention a "soybean seed" is one from which roots and shoots are able to grow. Reference to "seed" and "seeds" is used interchangeably herein and means viable soybean seeds to which compositions of the invention may be applied. Soybean seed as provided herein means seeds that are capable of germinating to at least conventional levels of germination typical of soybean seed.

Generally, the particles of use in seed coating compositions of the invention possess a volume mean diameter of a certain size as defined herein. To obtain particles of organic materials of a volume mean diameter applicable for use in the invention, organic materials in the form of, for example, 1 to 5 kilogram blocks or tablets may be broken up or kibbled into small millimeter-sized pieces (such as from 2 mm-8 mm approximate diameter in size, for example from 4 mm to 6 mm) in a kibbling machine. The millimeter-sized pieces can then be passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles can then be passed through a micronising apparatus, such as an AFG micronising air mill to obtain particles of a desired VMD range, such as from 15 µm-20 µm, that is of use in the present invention. The skilled addressee will appreciate that such procedures for obtaining small particles are well known in the art. Preferably, dry powder compositions of the invention comprise composite particles having a volume mean diameter of 5 µm, for example of 10 µm, 11 µm, 12 µm, 13 µm, 14 µm, 15 µm up to 40 µm or any value therein between. As stated herein, the volume mean diameter of the composite particles is typically $\geq 10$ µm or $\geq 12$ µm and may lie in the range from 5 µm to 200 µm and may have a value that lies anywhere therein between, for example from $\geq 10$ µm to 100 µm; or from $\geq 10$ µm to 40 µm; or from $\geq 10$ µm to 30 µm or any desired volume mean diameter value in between. Preferably, dry powder compositions of the invention comprise particles having a volume mean diameter of 10 µm, for example of 10 µm, 11 µm, 12 µm, 13 µm, 14 µm, 15 µm and the like up to any volume mean diameter of choice, such as up to 200 µm or any volume mean diameter in between for example 40 µm or 30 µm. Such compositions are considered to be less of a thoracic hazard to humans and are not thought to be allergenic.

The organic material used in the present invention is selected from organic materials that can be applied to soybean seeds either as a powder wherein the powder particles are of a pre-determined volume mean diameter (VMD) or the powder particles are applied in liquid form, such as an oleaginous formulation or as an aqueous formulation. In liquid formulations, particles of a pre-determined volume mean diameter are suspended therein in a suspension formulation and applied to the seeds which are then dried using conventional drying procedures. Preferably, the organic material is applied to soybean seeds in a dry powder form, the particles of the organic material may have a volume mean diameter of any conventional size as defined herein. Such organic materials include additives as herein defined and may include added further components such as added UV blockers or added antioxidants or the like. Dry powders of the present invention may be made up of one or more organic materials that have a melting point at or above 50° C. and which are of use in the present invention. Suitable organic materials of use in the invention include waxes having a melting point of ≥50° C., more preferably of ≥60° C., and most preferably are made up of hard waxes having a melting point of ≥70° C. Suitable organic materials are made up of particles of a size range as herein defined and may be selected from waxes such as carnauba wax, beeswax, Chinese wax, shellac wax, spermaceti wax, candelilla wax, castor wax, ouricury wax, and rice bran wax. Such waxes typically display a high enthalpy of lattice energy during melt. Preferably the organic material is carnauba wax which may be applied in liquid form, typically in the form of a suspension or powder form as discrete particles. Preferably, the organic material is applied in dry powder form to soybean seeds. The skilled addressee will appreciate that the actual VMD of particles of use in the invention that are used on soybean seed will be appropriate to the size of the seeds to which the particles are to be applied. Furthermore, the skilled addressee will also appreciate that where the VMD is defined as being ≥10 µm or ≥12 µm the size of the particles will be governed by the size of the seed to which it is applied and such a range should be construed as being commensurate therewith. Thus, the size range of particles of use in the invention is not open-ended in respect of an upper size limit but only insofar as such a limit is applicable to soybean seed to which particles of the invention may be expected to adhere as a coating. The limit in the sizing of the particles of use in seed coatings of the invention will be apparent to the skilled addressee.

The one or more additives for enhancing seedling vigour and/or seedling growth from soybean seeds may be selected from one or more inorganic or chemical additives and/or one or more live biological agents.

Suitable inorganic agents include commercially available NPK fertilisers that may be added to soybean seed coatings of the invention. These may be added in the form of dry powders of soluble ions that include the so-called primary macronutrients such as nitrogen, phosphorus, and potassium; the so-called secondary macronutrients such as calcium, sulphur, and magnesium; and the so-called "micronutrients" (trace minerals such as boron, chlorine, manganese, iron, zinc, copper, molybdenum, and selenium). "Macronutrients" are taken up in relatively large quantities and are present in plant tissue in quantities from about 0.2%-4% on a dry weight basis. "Micronutrients" are taken up in smaller quantities and are present in plant tissue in quantities measured in parts per million (ppm), ranging from about 5-200 ppm, or less than 0.02% dry weight.

Additives may be selected from bioregulators commonly applied in the art such as brassinosteroids, cytokinines e.g. kinetin or zeatin, the auxins e.g. indolylacetic acid or indolylacetyl aspartate, the flavonoids and isoflavanoids e.g. formononetin or diosmetin, the phytoaixins e.g. glyceolline, phytoalexin-inducing oligosaccharides such as pectin, chitin, chitosan, polygalacuronic acid and oligogalacturonic acid, compounds such as the gibellerins produced by rhizobial symbionts and endophytic microorganisms such as acetobacter diazotrophicus and herbaspitillum seropedicae and the like.

Species of mycorrhizal fungus are also capable of augmenting levels of available nutrients in the soil with further organic and inorganic nutrients that are assimilable by a crop plant.

Suitable species of mycorrhizal fungus include those that are capable of colonising a host plant's roots, either intracellularly as in arbuscular mycorrhizal fungi (AMF), or extracellularly as in ericoid mycorrhizal (EM) fungi.

Examples of AMF mycorrhizae of potential use in the invention include those from the *Glomus, Gigaspora, Acaulospora* and *Sclerocystis*. Suitable species include *Glomus fasciculatum, G. intraradices, G. claroideum; G. intra, G. clarum, G. brasilianum, G. deserticola, G. monosporus, G. mosseae, G. tortuosum, G, sinuosum, Gigaspora margarita, Gigaspora gigantean* and *Acaulospora longular.*

Ericoid mycorrhizas (EM) are known to have saprotrophic capabilities and these are thought to enable plants to receive nutrients from not-yet-decomposed materials via the decomposing actions of their ericoid partners. A suitable genus of EM of potential use in the invention is *Pezizella.*

Further species of bacteria and fungi of potential use are those that are able to act on inorganic and/or organic substrates to release compounds in soluble form from such substrates, such as phosphorus. Such species of bacteria include those from *Alcaligenes, Acinetobacter, Azospirillum, Bacillus, Enterobacter, Erwinia, Flavobacterium, Paenibacillus, Pseudomonas, Rhizobium, Burkholderia,* and *Serratia.* Examples of species of the *Bacillus* genus are *Bacillus megaterium, Bacillus coagulans*, species of the *Azospirillum* genus such as *Azospirillum brasilense*, species of the *Pseudomonas* genus, such as *Pseudomonas aeruginosa, Pseudomonas aurantiaca, Pseudomonas putida, Pseudomonas pseudoalcaligenes, Pseudomonas fluorescens, Pseudomonas poae,* and *Pseudomonas trivialis*, species of the *Rhizobium* genus such as *Bradyrhizobium* and *Rhizobium leguminosarum*, and species of the *Paenibacillus* genus (formerly considered as *Bacillus* genus) such as *Paenibacillus lautus.* Commonly used *Rhizobium inoculants* may be sourced from such companies as Becker Underwood and EMD Crop Bioscience.

A further live biological inoculant of use for soybean seed coating is *Trichoderma*, a fungus that is capable of making available, and in the adsorption of, mineral nutrients from the soil such as by solubilising unavailable phosphorus and zinc in the soil. Other capabilities of the fungus include the decomposition of organic matter thereby releasing calcium, potassium, and nitrogen available for plant use. By such capabilities certain *Trichoderma* species can be used to contribute to a balanced fertilisation of plants in the field and thereby the requirement for adding large amounts of artificial fertilisers may be reduced by as much as 50% depending on crop type. Suitable *Trichoderma* strains are known in the art, such as those known to the University of the Philippines Los Baños (UPLB), Institute of Biological Sciences.

Examples of additives for increasing fertiliser efficiency, plant productivity, growth, and nutrient accumulation may be sourced from such commercial sources as Incotec Inc., Germains, Bayer CropScience, and Becker Underwood. Suitable additives may be selected from commercially available products such as Auxigrow® (Auxein Corp., Lansing, Mich., USA) and Amisorb® (Donlar Corp., Chicago) or the so-called phytochelates described by A. M. Kinnersley in Plant Growth Regul. (1993), 12(3), 207-18, which are thought to influence the availability to the plant of minimal amounts of certain metals such as Zn, Fe, Cu and the like for optimal growth and productivity. Examples of the latter include polymers of L-lactic acid, L-lactoyllactic acid and water-soluble polyaspartates. Other additives that may be applied to soybean seed coatings of the invention include the kind of adjuvants that are found in conventional commercial agrochemical formulations. Suitable additives for inclusion into soybean seed coatings of the invention may be selected from those described by Chester L. Foy, Pestic. Sci. (1993) 38, pp. 65-76; and in EP 0357559. Seed coating compositions of the invention may further include conventional additives such as agents having wetting, dispersing and de-foaming modes of action. Suitable surface-active compounds are non-ionic, cationic and/or anionic surfactants having good emulsifying, dispersing and wetting properties. Such adjuvants for crop protection formulations are obtainable from fine chemicals producers [e.g. Clariant AG (Muttenz, Switzerland)] and include (fatty)alcohol alkylphenol ethoxylates, polyarylphenol ethoxylates, dispersing phosphates, taurides and/or alcohol monosuccinates. The term "surfactants" also comprises mixtures of two or more surfactants and natural or synthetic phospholipids of the cephatin and lecithin series, e.g. phosphatidyl-ethanolamine, phosphatidylserine, phosphatidylglycerol, lysolecithin sugar esters. A typical de-foaming agent is Fluowet PL80B® (Clariant AG) and typical antifreeze compounds are glycols and polyethylene glycols. Further ingredients may include solid or liquid substances ordinarily employed in formulation technology, e.g. natural or regenerated minerals, tackifiers, thickeners or binders. Other suitable additives are emulgating protein hydrolysates, e.g. as described in EP 0297426. Dyes often used in seed treatment compositions include water-insoluble or water-soluble dyes. Examples of dyes that may be added to compositions of the invention include Colanyl Red® (Clariant AG, Muttenz), Rhodamin B, white pigment (titanium dioxide) or Luconyl® (BASF AG). Altogether additives may be used to ensure that the formulation disperses well, does not settle or freeze and differentiates the seeds from untreated seeds. Other special additives which are known to enhance seedling vigour in particular in combination with certain pesticides, e.g. fungicides in combination with 3',4',5',6'-tetrachloro-2,4,5,7-tetraiodo-fluorescein (EP0297426), may be applied to the seeds in a combined amount that is effective, preferably synergistically effective, to increase seedling vigour and plant growth.

Additionally, the organic particles of use in compositions of the invention may contain other further components such as additives selected from UV blockers such as beta-carotene or p-amino benzoic acid, colouring agents such as optical brighteners and commercially available colouring agents such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled addressee will appreciate that the selection of such commonly included additives will be made depending on end purpose, and perceived need.

Seed compositions of the invention may be applied to soybean seed at a rate of application from 0.1 g to 500 g, preferably from 1 g to 100 g, most preferably from 5 g to 50 g of the active ingredient (a.i.) per 100 kg of seed.

Liquid formulations of the invention may be formulated as an aqueous formulation or as an oleaginous formulation, depending on design. Aqueous formulations may include surfactants selected from commercially available surfactants such as Tween 20, Silwet L77, Tween 80, Torpedo II, Newmans T80, Fortune, Guard, Rhino, Biopower, and the like.

Oleaginous formulations, that is to say oil-based formulations, may contain any oil suitable for use in the present invention which may be selected from petroleum oils, such as paraffin oil, and vegetable oils such as rapeseed oil, soybean oil, sunflower oil, palm oil and the like. Oil formulations of use in the invention contain organic particles of the invention and as described herein and these in turn may be admixed with flow agents such as hydrophilic precipitated silicas, for example Sipernat 383 DS, Sipernat 320, EXP 4350, and Sipernat D-17 and the like. Such free-flowing agents may be dispersed in oils, for example, for anti-foaming purposes.

The skilled addressee will appreciate that where an aqueous or an oil formulation may be used, the liquid element should be removed from the coated soybean seeds after coating is achieved, for example by drying off using conventional evaporative drying processes.

Coatings of organic materials of use in the present invention also serve to protect immediately planted soybean seeds from soil borne pathogens, that is to say, ones that are able to colonise the soybean seeds, such as the seed cuticle and/or ones that populate the soil and which are capable of acting on soybean seeds. Such soil borne pathogens are typically bacteria and/or fungi. Examples of soil borne bacterial and fungal pathogens that may attack soybean plants include *Rhizoctonia* spp. such as *R. solani*, *Aspergillus* spp., *Pythium* spp, *Sclerotium* spp. such as *S. rolfsii*, *Fusarium* spp., *Phytophthora* spp., *Alternaria* spp., and the like.

According to a further aspect of the invention there is provided use of organic material in the form of particles having a mean volume diameter for the manufacture of a coating composition as defined herein. The coating composition is a seed coating composition. The organic materials are selected from one or more organic materials having a melting point of ≥50° Centigrade, more preferably of ≥60° C. and most preferably are made up of hard waxes having a melting point of ≥70° C. Suitable organic materials include carnauba wax, beeswax, Chinese wax, shellac wax, spermaceti wax, candelilla wax, castor wax, ouricury wax, and rice bran wax or a mixture of one or more thereof, and preferably, the seed coating that is used includes carnauba wax. Preferably, in this aspect of the invention, the organic particles have a mean volume diameter of ≥5 μm, preferably selected from ≥10 μm to 200 μm, as herein described and as appropriate for the soybean seeds to which the particles are to be applied.

In a third aspect of the invention there is provided a method of manufacturing a soybean seed coating as herein described that comprises 1) selecting one or more solid organic materials having a melting point of ≥50° C.;

2) machining said organic material into particles of a desired mean volume diameter in the range from ≥5 μm; and 3) adding one or more additives for enhancing seedling vigour and/or seedling growth selected from one or more inorganic additives and/or one or more live biological agents.

The organic material in this aspect of the invention may be selected from organic materials and may be selected from organic waxes having a melting point of ≥50° C., more preferably of ≥60° C., and most preferably are made up of hard waxes having a melting point of ≥70° C. Suitable waxes for use in the invention include carnauba wax, beeswax, montan wax, Chinese wax, shellac wax, spermaceti wax, candelilla wax, castor wax, ouricury wax, and rice bran wax or a mixture of one or more thereof. Preferably, the selected organic material includes a substantial proportion of carnauba wax up to 100%, for example 1%, 10%, 20%, 30%, 40%, 50%, 60%, 70%, 80%, 90% or more or any proportion therein between, the rest being made up of at least one other organic material as herein defined. Preferably, the selected organic material is solely carnauba wax which may contain further added components as herein described, such as UV blockers, antioxidants such as vitamin E and the like.

The one or more additives for enhancing seedling vigour and/or seedling growth may be selected from one or more inorganic additives and/or one or more live biological agents as herein defined.

In a further aspect of the invention, there is provided a soybean seed coating composition produced by the method as described herein.

In a further aspect of the invention there is provided a coating composition as described herein for use on soybean seeds.

In a further aspect of the invention there is provided a method of coating soybean seeds with a coating composition that comprises at least one organic material wherein the organic material is selected from waxes having a melting point of ≥50° C., the method comprising i) obtaining a population of particles of wax admixed with additives as a population of separate particles of a pre-determined VMD; and ii) applying the said population of particles to soybean seeds.

The skilled addressee will appreciate that environmental factors that may affect soybean seed viability includes such factors as extremes of heat, loss of moisture and the presence of pathogens such as bacteria and/or fungi. The skilled addressee will also appreciate that the pre-determined VMD will be appropriate to the size of the soybean seed to which the coating is to be applied.

In a variant of this aspect of the invention there is provided a method of coating soybean seed with a coating composition that comprises an organic material that is selected from waxes having a melting point of ≥50° Centigrade, the method comprising i) obtaining organic material;

ii) heating the organic material so as to form a liquid phase or a gaseous phase;

iii) cooling the liquid phase or gaseous phase of ii) to below the melting point of the organic material, forming a solid;

iv) adding one or more additives to the solid formed in iii);

v) machining the solid organic material of iii) into particles of a pre-determined VMD as herein defined; and vi) applying the particles of v) to soybean seeds.

In a second variant of the above aspect of the invention there is provided a method of coating soybean seed with a coating composition of the invention that comprises an organic material material that is selected from waxes having a melting point of ≥50° Centigrade, the method comprising i) obtaining said organic material;

ii) heating the organic material so as to form a liquid phase or a gaseous phase;

iii) adding one or more additives to the liquid phase or gaseous phase of ii);

iv) cooling the liquid phase or gaseous phase of iii) to below the melting point of the organic material, forming a solid;

v) machining the solid organic material of iv) into particles of a pre-determined VMD as herein defined; and vi) applying the particles of iv) to soybean seeds.

The organic material of use in the invention may comprise one or more organic materials selected from organic materials as herein defined. Preferably, the organic material is carnauba wax. Where two or more organic materials of use in the invention are employed as the organic material in a seed coating composition of the invention they may be heated together so as to form a liquid phase or a gaseous phase during which phases the organic material may be mixed, if required. Once the organic materials are mixed they may be cooled to below the melting point of the organic material possessing the lowest melting point in the liquid phase (where a gas phase is employed, this will be cooled to a liquid phase), forming a solid which may then be machined, such as by comminution, into particles of a pre-determined VMD as herein defined using conventional procedures. As described above, one or more additives may be added to the organic materials at points indicated above. It will be appreciated that the person skilled in the art will understand at what point or points in the described processes additives may be added to the organic material, depending on the additive material to be added to the organic material forming particles of use in the invention. Once the organic material is in the form of particles of a known VMD, the particles may be applied to soybean seed using conventional means, such as by tumbling in seed coating drums and the like.

The treatment composition is applied to the soybean seed in dry particulate form or liquid form as hereinbefore described, and preferably in dry particulate form. The organic carrier material in the above aspect and variant aspect of the invention may be selected from organic materials selected from organic waxes having a melting point of ≥50° C., more preferably of ≥60° C., and most preferably are made up of hard waxes having a melting point of ≥70° C. Suitable waxes for use in the invention include carnauba wax, beeswax, Chinese wax, shellac wax, spermaceti wax, candelilla wax, castor wax, ouricury wax, and rice bran wax or a mixture of one or more thereof. Preferably, the selected organic material includes a substantial proportion of carnauba wax up to 100%, for example 1%, 10%, 20%, 30%, 40%, 50%, 60%, 70%, 80%, 90% or more or any proportion therein between as herein described, the rest being made up of at least one other organic material as herein defined. Preferably, the selected organic material is solely carnauba wax which may contain further additives as herein defined.

Generally, the particles of use in the above aspect of the invention and the accompanying variant aspects of the invention possess a volume mean diameter of ≥10 μm, such as ≥12 μm such as in the range of from ≥10 μm to 200 μm, for example from ≥10 μm to 100 μm; or from ≥10 μm to 40 μm; or from ≥10 μm to 30 μm or any desired volume mean diameter value in between. Preferably, dry powder compositions of the invention comprise particles having a volume mean diameter of 10 μm, for example of 10 μm, 11 μm, 12 μm, 13 μm, 14 μm, 15 μm and the like up to any volume mean diameter of choice, such as up to 200 μm or any volume mean diameter in between for example 40 μm or 30 μm. More preferably compositions of the invention comprise particles having a volume mean diameter of from about 12 μm to 200 μm.

There now follow examples that illustrate the invention. It is to be understood that the examples are not to be construed as limiting the invention in any way.

EXAMPLE: GROWTH AND VIGOUR IN *GLYCINE MAX*

Glycine max seed provided by Herbiseeds (Twyford, UK)
Combination of Carnauba Wax Particles and Inoculant
Dry Powder Formulation of Rhizobium Welsh Plant Breeding Station (WPBS) *Rhizobium* Collection

*Rhizobium* concentration is measured by diluting 1 gm in 1 l of water, before further diluting by taking 1 ml of the suspension and making it up to 1000 ml. A 20 μl sample is then added to an Improved Neubauer Counting Slide and a count made of 4 large squares (0.1 mm^3) in both of the grids. The mean for each square is calculated and the mean of the two grids used to produce a measurement of spores per 100 nl of water. The dilution factor is then applied to produce an approximation of the number of spores per gram.

Carnauba Wax Particle Sizing

Steps in Air Milling in Boyes Micronisation Process (for carnauba wax particles with a VMD of approx. 16 μm)

1. 2 kg carnauba wax blocks are first kibbled into approximately 4 to 6 mm pieces in a KT Handling Ltd Model 04 kibbler (serial no. 729/C) following the manufacturer's instructions.

2. The kibbled pieces are then passed through an Apex Construction Ltd Model 314.2 Comminuting Mill (serial no. A21306) and reduced further in size to a range of 250 to 300 um.

3. The comminuted particles are then passed through a Hosokawa Micron Ltd Alpine 100AFG jet mill (serial no. 168092) following the manufacturer's instructions, setting the mill at a speed of 8000 rpm for particles having a VMD of approx. 16 μm, with a positive system pressure of 0.03 bar.

4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of approx. 16 um.

Carnauba wax particles (VMD of 16 μm) are combined with at a ratio of 1:3 (*Rhizobium*:Carnauba wax particles) in a 50 ml tube using a Stuart roller mixer set at 25 rpm for 5 minutes. This can then be used to calculate the quantity of spore/Carnauba wax particles powder mix required for the seed coating based on a standard of $1 \times 10^9$ spores gram$^{-1}$ of seed.

A homogeneous mix of is attained through tumbling seed and carnauba wax formulation in a cylinder, adapted to produce lateral mixing/tumbling through the inclusion of angled interior vanes, placed on a Wheaton roller for 5 minutes.

Rock Phosphate

Rock Phosphate (Garden Direct, UK) with a 30% $P_2O_5$ content is crushed using a pestle and mortar and then passed through a 32 micron mesh sieve.

This is combined with Carnauba wax particles which were sized following the protocol described above with the exception that the milling speed was set at 2500 rpm to obtain a VMD of 75 μm at a ratio of 1:3 (Rock Phosphate: Carnauba wax particles). A homogeneous mix of is attained through tumbling seed and carnauba wax formulation in a cylinder, adapted to produce lateral mixing/tumbling through the inclusion of angled interior vanes, placed on a Wheaton roller for 5 minutes.

Chitosan Chitosan (>75% Deacetylated chitin, Poly(D-glucosamine)) (Sigma Aldrich, UK) is crushed using a pestle and mortar and then passed through a 32 micron mesh sieve.

This is combined with Carnauba wax particles (VMD 75 μm) at a ratio of 1:19 (Chitosan:Carnauba wax particles). A homogeneous mix of is attained through tumbling seed and carnauba wax formulation in a cylinder, adapted to produce lateral mixing/tumbling through the inclusion of angled interior vanes, placed on a Wheaton roller for 5 minutes.

Treatments:
1. Carnauba wax particles and *Rhizobium*
2. Carnauba wax particles and Rock Phosphate
3. Carnauba wax particles and Chitosan
4. *Rhizobium* control
5. Rock Phosphate control
6. Chitosan control
7. Carnauba wax particle control (vehicle control)
8. Untreated Control Seeds are planted in two 84 well plug trays using moist seed potting compost (John Innes No. 2). The trays are placed in a Vitopod propagator (Greenhouse Sensations, UK) at 25° C. Moisture content (Brannan Soil Moisture Meter, Fisher Scientific, UK) and pH levels (Brannan Soil pH meter, Fisher Scientific, UK) are checked to ensure that the conditions are consistent across the tray. The order of the treatments is randomised (by row units) to reduce any unforeseen bias.

At the true leaf stage the plants are carefully transplanted from the plugs to 7 cm square pots filled with a sterilised top soil. The macro-nutrient (nitrates, phosphates and potassium) content of the top soil is measured using a La Motte Model STH-4 soil testing kit and recorded. Six replicates for each treatment (48 plants) are randomly assigned to each of three propagators, and further randomised within the propagator (total=144 plants). The propagators are set at 19° C., 25° C. and 31° C. Light is provided on a 16:8 Light:Dark cycle using a twin bulb T5 lighting array suspended 150 mm above the propagator (Lightwave T5, 48 w, 3300 lumens). T5 tubes (6500 Kelvin) deliver the bright blue/white light required by the plant for growth without emitting much heat which may scorch tender seedlings Moisture content and pH levels are checked to ensure that the conditions are consistent across the propagator by measuring six random plants along a pathway (alternating between a W and Z). This is repeated for each propagator.

Plants are watered as required based on conditions to maintain consistent soil moisture content of 18% throughout all plants.

The lids of the propagators are removed at such time as required due to the plant height.

After 21 days the plants are removed from the propagators and the following measurements recorded:
Root weight (fresh)
Shoot weight (fresh)
Root nodule formation Plant tissue is measured for macro-nutrient content using the instructions provided with a La Motte Model PT-3R Plant Tissue Test kit.

Analysis

The influence of the factors and their interactions are tested with a 2-way ANOVA. The analysis was done for each temperature separately and with temperature as a factor. For the ANOVA with temperature as a factor, treatments were used as a sub-plot factor. Fisher's Least Significance Differences were calculated at the 5% significance level to compare treatment means. Shapiro-Wilks's test was performed to test for non-normality.

Delivery of Macronutrients Using Carnauba Wax Particles as a Seed Coating on Soybean Aim: to assess the potential for formulating essential macronutrients into carnauba wax particles and using this as a seed coating to provide the germinating seed and seedling with supplementary nutrients to aid in early stage growth.

Macronutrients Selected:

Phosphorus (P)

- Phosphorus (P) is an essential part of the process of photosynthesis.
- Involved in the formation of all oils, sugars, starches, etc.
- Helps with the transformation of solar energy into chemical energy; proper plant maturation; withstanding stress.
- Effects rapid growth.
- Encourages blooming and root growth.

Potassium (K)

- Potassium is absorbed by plants in larger amounts than any other mineral element except nitrogen and, in some cases, calcium.
- Helps in the building of protein, photosynthesis, fruit quality and reduction of diseases.
- Potassium is supplied to plants by soil minerals, organic materials, and fertilizer.

Both Potassium and Phosphorus can be found in soluble form in Monobasic Potassium Phosphate or MKP($KH_2PO_4$), a soluble salt commonly used as a fertiliser and plant growth supplement.

Formulation Method

Carnauba is heated on a hotplate at 100° C. to a molten state. Monopotassium phosphate (MKP) is dissolved in deionised water to the required concentration. The MKP solution is slowly added to the molten wax under stirring at 1500 rpm. Stirring continues for 5 minutes before the water/wax emulsion is poured onto a metal sheet to cool. The resulting solid wax including micro-droplets of MKP is then micronized in an air mill to a VMD of approx. 10.3.

Carnauba Wax Sizing Method

Steps in Air Milling in Boyes Micronisation Process (for carnauba wax particles with a VMD of approx. 10.3 μm)

1. 2 kg carnauba wax blocks are first kibbled into approximately 4 to 6 mm pieces in a KT Handling Ltd Model 04 kibbler (serial no. 729/C) following the manufacturer's instructions.

2. The kibbled pieces are then passed through an Apex Construction Ltd Model 314.2 Comminuting Mill (serial no. A21306) and reduced further in size to a range of 250 to 300 um.

3. The comminuted particles are then passed through a Hosokawa Micron Ltd Alpine 100AFG jet mill (serial no. 168092) following the manufacturer's instructions, setting the mill at a speed of 12,500 rpm with a positive system pressure of 0.03 bar.

4. The grinding air is to be kept to 6 bar, the system rinsing air flow and Classifying Wheel gap rinsing air are both to be set at a minimum of 0.5 bar and no more than 0.75 bar, the cleaning air filter is to register a delta of no more than 5 bar to achieve a final particle size with a VMD of approx. 10.3 um.

Experimental Method

Wax particles containing 10% MKP are added to 10 g of Soybean seed, cv. Pripyat (Soya UK, Hampshire) at loadings of 0.1% and 1% by mass. Seed is well mixed to ensure a homogenous distribution across the seed. A third batch of seed is combined with unformulated carnauba wax particles as a control.

10 seeds for each treatment are sown in 20 cell modular seed trays with an individual cell size: Length 37 mm×Width 37 mm×Depth 65 mm, with each tray representing a single sample. Each treatment is replicated four times.

The pots are filled with a sieved, heat-sterilised seed mix (Levingtons F1 Seed and Modular Compost—Low Nutrient)) to level with the top of the cell. Low Conductivity: 250-280 μS, Standard pH: 5.3-5.7, Mg/liter added: N-100, P-200, K-200.

They are then lightly tamped and 30 ml of deionised water added to each cell through a course filter. A single seed is then placed on the surface of the soil and covered with a thin layer of vermiculite to a depth of 2-3× the diameter of the seed, as per supplier recommendation. The trays are placed within plastic gravel trays (two per tray) which are lined with capillary matting to aid watering.

The gravel trays are then placed in a thermostatically controlled plant growth chamber (Fitotron SGC120, Weiss Gallenkamp, Loughborough, UK). Temperature cycling is set at 20° C./10° C. on a 16/8 hr schedule. Lighting at 150 $\mu mol\ m^{-2\ s-1}$ on a 16/8 hr photoperiod is introduced at first emergence.

Plants are watered daily from the bottom in order to maintain a compost moisture level of approximately 40% in the cells After 10 days the plants are removed from the individual cells and the compost mix separated from the root structure. Plants from each 10 cell tray are combined and separated into shoots, made up of the first true leaves and growing tip, and roots.

Plant Tissue Analysis: (Conducted to the Following Method by NRM Laboratories (Bracknell, UK)

Total Phosphorus (P), Potassium (K), Magnesium (Mg), Calcium (Ca), Sodium (Na), Manganese (Mn), Copper (Cu), Iron (Fe), Zinc (Zn), Boron (B) determination using Inductively Coupled Plasma-Optical Emission Spectroscopy (ICP-OES) method Equipment 1. ICP Emission Spectrograph
2. Autosampler
3. Digital Dilutor Reagents 1. 3N Hydrochloric Acid: Dilute 250 ml. of concentrated hydrochloric acid to 1 liter using deionized water and mix well.
2. Nitric Acid: $HNO_3$ Standards 1. Stock Solutions: Use 1000 PPM certified, NIST traceable, plasma grade standards for the 16 listed elements.
2. Instrument Calibration Standards:
   a. WAT 1-deionized water
   b. WAT 2—Mn, Fe, Al, B, Cu, Zn, Na, Pb, Cd, Ni, Cr, Mo—Pipet 10 ml. of stock solution of each element into a 1 liter volumetric flask. Add 5 ml. of nitric acid. Dilute to volume with deionized water and mix well.

c. PLN2—P, K, Ca, Mg—Pipet the designated ml. of stock solution into a 1 liter volumetric flask. Add 5 ml. of nitric acid. Dilute to volume with deionized water and mix well.

| Element | Stock Solution ml. | Final Concentration ppm. | Instrument Readout % |
|---|---|---|---|
| P | 10 | 10 | 1.00 |
| K | 50 | 50 | 5.00 |
| Ca | 20 | 20 | 2.00 |
| Mg | 10 | 10 | 1.00 |

3. Instrument Calibration Verification Standards:
   a. A second set of calibration standards obtained from a different manufacturer.

Sample Preparation

Samples are dried and ground to pass through a 1 mm screen.

The elements in the residue remaining after the destruction of the organic matter by ashing at 550° C. are dissolved in hydrochloric acid:
1. Dry Ash
   a. Weigh 1 g sample into a 10 ml. glazed, high-form porcelain crucible.
   b. Ash in a muffle furnace for 4 hours at 500 C.
   c. Let cool and add 5 ml. of 3N HCl.
   d. Place on a hot plate and boil gently for 5 minutes.
   e. Let cool and transfer to a 100 ml. volumetric flask. Dilute to volume with deionized water and mix well. Use this solution for the analysis of Mn, Fe, Al, B, Cu, Zn, Na, Pb, Cd, Ni, Cr and Mo.
   f. Dilute the solution obtained in 1e. one to ten with deionized water using a digital dilutor. Use this solution for the analysis of P, K, Ca and Mg.

ICP Procedure
1. Set up and operate the ICP Emission Spectrograph in accordance with manufacturer's specifications.
2. Mn, Fe, B, Cu, Zn, Na, Ni analysis.
   a. Choose PLANT from the method menu.
   b. Calibrate the instrument using WAT1 and WAT2 instrument calibration standards.
   c. Analyze the sample digests obtained in 1e. of the sample preparation section.
3. P, K, Ca, Mg analysis.
   a. Choose PLANTDIL from the method menu.
   b. Calibrate the instrument using WAT1 and PLN2 instrument calibration standards.
   c. Analyze the digests obtained in 1 f. of the sample preparation section.

Quality Control
1. Following calibration, analyze one high instrument calibration standard, one instrument calibration verification standard and one quality control sample.
   a. Instrument Calibration Standard: Values must be within 3% of the known value for K and Mo. All other elements must be within 2% of the known value.
   b. Instrument Calibration Verification Standard: Values must be within 10% of the certified values.
   c. Quality Control Sample: Values for all elements must be within limits established by the Extension chemist.
2. Analyze a high instrument calibration standard after each tenth sample and at the end of the set of samples.
   a. Values must be within 8% of the known values.
   b. If any of the values are greater than 8% from the known values, recalibrate the instrument and begin sample analysis from the last "good" instrument calibration standard.
3. Prepare one duplicate sample for each 10 samples. If the set contains less than 10 samples, prepare one duplicate per set.
   a. Results on the duplicate sample should agree within 20% of the average value of the two samples.

REFERENCES

1. Isaac, R. A. and W. C. Johnson, 1985, *Elemental Analysis of Plant Tissue by Plasma Emission Spectroscopy: Collaborative Study*. JAOAC. 68(3), pp 499-505.
2. AOAC Official Method 985.01, in *Official Methods of Analysis of AOAC International*, 16th edition, Volume I Chapter 3, p. 4.
3. AOAC Official Method 968.08 D(a), in *Official Methods of Analysis of AOAC International*, 16th edition, Volume I Chapter 4, p. 23.

Phosphate Solubilisation using Beneficial Microbes

Several bacterial species are able to impart a beneficial effect upon plant growth. Mostly they are associated with the plant rhizosphere, so they are called as rhizobacteria. This group of bacteria has been termed plant growth promoting rhizobacteria, and among them are strains from genera such as *Alcaligenes, Acinetobacter, Arthrobacter, Azospirillum, Bacillus, Burkholderia, Enterobacter, Erwinia, Flavobacterium, Paenibacillus, Pseudomonas, Rhizobium,* and *Serratia*.

The production of organic acids by phosphate solubilizing bacteria has been well documented and identified as the main mechanism for phosphate solubilisation. Gluconic acid seems to be the most frequent agent of phosphate solubilisation (*Pseudomonas* sp.), and 2-ketogluconic acid is also identified in strains with phosphate solubilizing ability (*Rhizobium* sp.).

Saprophytic fungi are also known to solubilise both organic and inorganic phosphates. Several genus, including *Trichoderma, Penicillium,* and *Gliocladium* have exhibited potential as biofertilisers. Morales et al (2011) demonstrated that *Penicillium albidum* was able to solubilise 64 mg of organic/inorganic phosphate per gram of fungi.

Experiment to Assess the Potential for Delivery of Phosphate Solubilising Organisms as a Seed Costing Using Carnauba Wax Particles Using a dry spore powder of a phosphate solubilising organism, such as *Penicillium bilaii*.

Spores are combined with carnauba wax particles with a VMD of approximately 10 µm at a ratio of 1:3. The powders are agitated to create a homogenous mix and applied to sterilised soybean seed at a loading of 0.1% (by mass). Additional batches of seed are treated with spores only (0.1%), Entostat only (0.1%) and untreated seed.

Phosphate Solubilising Activity Screening

Plate screening using Pikovskays' medium (see below) is used to demonstrate phosphate solubilising activity of the treated seed. 9 cm petri dishes are divided into quadrants and a seed is placed in the centre of each quadrant. Plates are incubated at 20° C. for 4 days.

Active phosphate solubilising agents produce clear zones around the seed as they solubilise the insoluble mineral phosphates within the media. The radius of the clear zones is measured and compared to the mean results achieved for each treatment. Differences are analysed using one-way ANOVA and Tukey Post-Hoc diagnostic test where significance is found.

Phosphate Uptake by Plant

Seeds are treated as described above.

$Ca_3(PO_4)_2$ is used as a source of insoluble phosphate.

Sure to Grow PET grow cubes (25×25×38 mm) are soaked in deionised water containing 1% $Ca_3(PO_4)_2$ in suspension until saturated. Cubes are placed in free draining plant trays on a level surface to prevent nutrient run-off and migration whilst taking care to avoid pooling of water at the root zone. 10 cubes are used per tray and the mean of these represents one replicate. Each treatment is replicated 8 times.

A single soybean seed is placed in the cross-cut X in the top of each cube. Seed trays are then covered to maintain a humid environment and regularly top watered with the 1% $Ca_3(PO_4)_2$ suspension to maintain a moist cube. Trays are incubated at 20° C. and 10° C. on a 16/8 hr thermal cycle. On germination the cover is removed and the seedling exposed to lighting on a 16/8 hr photoperiod.

After 15 days the plants are removed from the grow cube and nutrient content of the plant tissue is analysed using the ICP method described above.

Differences in the Phosphate content between treatments are assessed statistically using one-way ANOVA.

| Pikovskays' Medium | |
| --- | --- |
| Components | Quantities (g $l^{-1}$) |
| Glucose | 10 |
| $Ca_3(PO_4)_2$ | 5 |
| $(NH_4)_2SO_4$ | 0.5 |
| NaCl | 0.2 |
| $MgSO_4 \cdot 7H_2O$ | 0.1 |
| KCl | 0.2 |
| Yeast Extract | 0.5 |
| $MnSO_4 \cdot H_2O$ | 0.002 |
| $FeSO_4 \cdot 7H_2O$ | 0.002 |
| pH | 7.0 |

The invention claimed is:

1. A coating composition for effective application to and retention on soybean seed as a dry powder, consisting of: particles, said particles consisting essentially of:

i) at least one organic material selected from waxes having a melting point of >50° C., wherein the wax is in the form of particles having a volume mean diameter in the range of 5 μm to 200 μm; and ii) at least one additive for enhancing seedling vigour and/or seedling growth from soybean seeds wherein the at least one additive is selected from one or more inorganic additives and/or one or more live biological agents, wherein said particles adhere to said soybean seed by electrostatic charge without the use of a binder between said particles and soybean seed.

2. The coating composition according to claim 1, wherein the organic material is selected from waxes such as carnauba wax, beeswax, Chinese wax, shellac wax, spermaceti wax, candelilla wax, castor wax, ouricury wax, and rice bran wax; or a mixture of two or more thereof.

3. The coating composition according to claim 1, wherein the wax is carnauba wax.

4. A soybean seed comprising a coating composition according to claim 1.

5. A soybean seed comprising a coating composition according to claim 1, wherein the organic material is in dry particulate form.

6. A dry powder coating composition for effective application to and retention on soybean seed without the use of a binder between the powder and seed, said dry powder consisting of:

a plurality of dry particles, each said particles consisting essentially of:

at least one organic material selected from waxes having a melting point of ≥50° C., wherein the wax is in the form of particles having a volume mean diameter in the range of 5 μm to 200 μm;

at least one additive for enhancing seedling vigour and/or seedling growth from soybean seeds wherein the at least one additive is selected from one or more inorganic additives and/or one or more live biological agents; and an electrostatic charge operative to adhere the dry particles to the soybean seed.

* * * * *